(12) United States Patent
Rovaniemi et al.

(10) Patent No.: US 8,652,608 B2
(45) Date of Patent: Feb. 18, 2014

(54) FLOOR MAT

(75) Inventors: Rolf Rovaniemi, Rimforsa (SE); Stefan Ekdahl, Vikingstad (SE)

(73) Assignee: Absorbest AB, Kisa (SE)

( * ) Notice: Subject to any disclaimer, the term of this patent is extended or adjusted under 35 U.S.C. 154(b) by 211 days.

(21) Appl. No.: 13/201,588

(22) PCT Filed: Feb. 17, 2010

(86) PCT No.: PCT/EP2010/051979
§ 371 (c)(1),
(2), (4) Date: Aug. 15, 2011

(87) PCT Pub. No.: WO2010/094703
PCT Pub. Date: Aug. 26, 2010

(65) Prior Publication Data
US 2011/0300340 A1  Dec. 8, 2011

(30) Foreign Application Priority Data

Feb. 20, 2009  (DE) .......................... 10 2009 001 059

(51) Int. Cl.
*B32B 3/26*  (2006.01)

(52) U.S. Cl.
USPC ............................................. 428/76; 428/172

(58) Field of Classification Search
USPC ..................................................... 428/76, 172
See application file for complete search history.

(56) References Cited

U.S. PATENT DOCUMENTS

| 5,938,650 A | 8/1999 | Baer et al. |
| 2010/0036345 A1 | 2/2010 | Rovaniemi |

OTHER PUBLICATIONS

International Search Report, PCT/EP2010/051979 (Jun. 23, 2010).

*Primary Examiner* — Alexander Thomas
(74) *Attorney, Agent, or Firm* — The Maxham Firm

(57) ABSTRACT

Floor mats for absorbing liquids, comprising a shell having a first and a second portion connected to each other in such a way that the first and the second portions of the shell form a pocket, and an absorbent material, which is a superabsorbent material is arranged in the pocket. The first and/or the second portion of the shell has a length in a range of 200 mm to 1000 mm and a width in a range of 200 mm to 600 mm, wherein the floor mat comprises three sections having a first thickness and two sections having a second thickness, wherein the second thickness is less than the first thickness.

13 Claims, 2 Drawing Sheets

FLOOR MAT

The present invention concerns a floor mat for absorbing fluids comprising a shell of a flexible non-woven spunbond fabric, wherein the shell has a first and a second portion, wherein the first and the second portions of the shell are connected together portion-wise in such a way that they form a pocket, and at least one absorbent material portion comprising a superabsorbent material, wherein the absorbent material portion is arranged in the pocket.

During medical operations in an operating room body fluids frequently flow out of the operating wound of the patient and go onto the floor around the operating table. Added to that there are also fluids which are not body-specific and which are required during the operation, for example for swabbing off the wound. Such accumulations of fluid on the floor around the operating table are a not inconsiderable safety risk as they make the floor smooth and slippery. In addition the fluids which are produced to a not inconsiderable extent in particular during an operation lasting for several hours have to be picked up from the floor after the operation and the floor then has to be cleaned in a complicated and costly procedure.

Therefore floor mats are known from the state of the art, in particular for operating rooms, which are arranged around the operating table during an operation to absorb and bind the fluids involved and which can be disposed of after the operation so that the floor can be subsequently cleaned using simple means.

The floor mats known from the state of the art however are of a comparatively small area and allow only point coverage of certain portions around the operating table.

In addition the floor mats known from the state of the art are only available with given predetermined absorption capacities. When the absorption capacity of a floor mat is exhausted during an operation the mat has to be replaced or the further fluids wet the surface of the floor, with the above-mentioned adverse consequences.

In comparison the object of the present invention is to provide a floor mat which avoids the aforementioned disadvantages and permits more flexible use of the mat.

At least one of the aforementioned objects is attained by a floor mat for absorbing fluids comprising a shell (4) of a flexible non-woven spunbond fabric, wherein the shell (4) has a first and a second portion, wherein the first and the second portions of the shell (4) are connected together portion-wise in such a way that they form a pocket, and at least one absorbent material portion comprising a superabsorbent material, wherein the absorbent material portion is arranged in the pocket, wherein the first and/or the second portion of the shell are of a length in a range of between 200 mm and 1000 mm and a width in a range of between 200 mm and 600 mm, wherein the floor mat has at least two portions of a first thickness and at least one portion of a second thickness, wherein the second thickness is less than the first thickness and wherein the portion of the second thickness is so arranged between the portions of the first thickness that it forms a fold line so that the two portions of the floor mat are pivotable towards each other.

Such a floor mat according to the invention with its segment-like structure permits flexible use of the floor mat both in regard to the area to be covered and also in regard to the required absorption capacity at the location at which the mat is laid. Because two respective segments of the floor mat can be easily folded onto each other along the fold line formed by a portion of reduced thickness the absorption capability of the mat at a given point can be increased by the user. If for example it is to be expected that large amounts of fluid will occur at a given location within the operating room, then at the beginning of the operation the mat according to the invention can be laid on the floor there, in which case two or more segments of the mat are placed one upon the other along the fold edges. There is also the possibility of the mat firstly being laid out in the non-folded condition and then being folded during the operation when a relatively large amount of fluid occurs at a given point so that the absorption capacity of the mat can be increased at that location.

In addition, particularly when the fold edge does not extend at a right angle relative to the longitudinal sides of the mat, the fold edge makes it possible to adapt the mat to the local aspects of the operating room, for example the mat can be arranged in a U-shape or O-shape around the foot of the operating table.

In cross-section the structure of the floor mat in its absorbent regions is preferably of a three-layer nature, wherein a shell encloses the absorbent material portion. The shell is formed by a first upper material portion and a second lower material portion which are so connected together that they form a closed pocket in their interior.

In that case the first and second portions of the shell, in an embodiment, can be of a one-piece nature, wherein the two portions are produced by a single sheet of material being folded along a fold line and the resulting portions being laid one upon the other. In that way the one side of the pocket to be formed is already closed off while only the other three sides still have to be closed by a seam.

In a preferred embodiment however the first and second portions of the shell comprise two mutually separate material portions, preferably of the same area, which are laid one upon the other and so joined together that they form a closed pocket in their interior. In that case the first and second portions of the shell are preferably joined along a closed line at the edge of the surface of the material portions. Joining of the two material portions forming the shell, that is to say production of the seam, is preferably effected by adhesive, by ultrasound welding or other welding or by a thread seam.

A flexible non-woven spunbond fabric in accordance with the present invention is a textile material produced from individual polymer fibers or filaments by thermal and pressure treatment. Such a material as the shell has the advantage that it allows through the fluids to the absorbent material portion arranged in the shell while it acts as a filter for coarser, non-fluid excretions so that they are held behind on the surface of the shell. Blockage of the absorbent material in the interior of the shell is prevented.

The first and/or the second portions of the shell are of a length in a range of between 200 mm and 1000 mm and a width in a range of between 200 mm and 600 mm. As the length and width of the overall mat is determined by the length and width of the shell those are also the preferred outside dimensions of the floor mat. Such dimensions can be readily handled in the operating room.

A particularly preferred embodiment is one in which the floor mat measures 370 mm×730 mm. In contrast for example to floor mats having a shell of felt material, in the case of the floor mat according to the invention, under a treading loading thereon, fluid possibly issues from the shell. It is therefore a matter of providing a mat with dimensions, which can be so positioned in the operating room that it permits effective absorption of the fluids involved without the mat being walked upon by the operating room personnel during the operation. Therefore widths of up to a maximum of 50 cm and lengths of up to a maximum of 80 cm have proven to be advantageous. Lengths of less than 40 cm and widths of less than 30 cm are found to be excessively small to ensure effective absorption of the fluids in the operating room.

In an embodiment each of the absorbent material portions is of a width in a range of between 160 mm and 540 mm and a length of between 160 mm and 960 mm.

In an embodiment the portion of the second reduced thickness which forms the fold line can be afforded by the finished floor mat which already includes the absorbent material portion in the pocket being subjected to a pressure and/or heat treatment in that fold line-forming portion so that the thickness thereof is reduced in that region. That can be effected for example by impressing with a heated punch.

In a particularly preferred embodiment the first and second portions of the shell are at least portion-wise connected together in such a way that they form the portion of the floor mat of the second thickness and thus the shell has at least two pockets, wherein an absorbent material portion is arranged in each of the pockets. Breaking down the absorbent material portion into two or more elements makes it possible for the floor mat to be markedly thinner structure in the fold region than in the other regions of the mat. For that purpose the first and second portions of the shell are joined together not only near the end along lines parallel to the outside edges but in addition also along a line which divides the floor mat into two portions.

In a preferred embodiment the floor mat has precisely three portions of the first thickness, that is to say those which contain the absorbent material, and two portions of the second thickness so that the three portions of the first thickness are pivotable towards each other.

It is desirable if in an embodiment the three portions of the floor mat of the first thickness are respectively of a substantially rectangular shape with a narrow side and a wide side, wherein the three portions with at least one of their narrow sides adjoin a portion of the floor mat of the second thickness, which forms a fold line. In that way the individual segments of the floor mat can be pivoted towards each other along their narrow sides and folded onto each other.

In an embodiment of the invention the absorbent material portion is a cellulose-containing material portion in which particles of a superabsorbent material are incorporated.

A superabsorbent material in accordance with the present invention is a polymer which is capable of absorbing a multiple of its own weight of fluids, for example up to 1,000 times when absorbing water. Chemically such a superabsorber is preferably a copolymer of acrylic acid (propenic acid, $C_3H_4O_2$) and sodium acrylate (sodium salt of acrylic acid, $NaC_3H_3O_2$), wherein the ratio of the two monomers to each other can vary. In addition there can be a so-called nuclear crosslinker which connects the long-chain polymer molecules formed together in place-wise relationship by chemical bridges. An alternative superabsorbent material which can be used is modified carboxymethyl cellulose (English abbreviation: CMC).

In an embodiment of the invention the absorbent material portion has an absorption capacity measured in accordance with DIN 11948-1 in a range of between 0.4 ml/cm$^2$ and 3.0 ml/cm$^2$ and preferably in a range of between 0.6 ml/cm$^2$ and 1.5 ml/cm$^2$.

In an embodiment of the invention the first thickness of the floor mat measured in accordance with the standards of the European Norm EN 12625-3:1999 is in a range of between 0.8 mm and 4 mm. In that respect a preferred embodiment of the invention is one in which the second thickness of floor mat measured in accordance with the standards of the European Norm EN 12625-3:1999 is in a range of between 0.2 mm and 0.8 mm.

In particular embodiments which involve a thickness ratio between the first and second thickness, measured in accordance with the standards of the European Norm EN 12625-3:1999 of between 1.5:1 and 20:1 and preferably 4:1 have proven to be advantageous as they permit the individual segments of the floor mat to be easily folded over and also laid one upon the other.

The structure of the floor mat according to the invention is explained once again hereinafter by means of a preferred embodiment of the production process. To produce a floor mat according to the invention firstly the starting materials, that is to say the first and second portions of the shell and the absorbent material portion, are provided on three mutually separate rolls. The first material portion of the shell, here the lower portion of the shell, is unrolled and coated with adhesive by means of an adhesive gun in those regions in which the first portion is to be joined to the second portion. In that case preferably those portions of the first material portion in which the absorbent material portions are to be accommodated, that is to say which later form the pockets, are not coated with adhesive. Subsequently, separated from the roll with the absorbent material are material portions which in respect of their size precisely match the portions of the first material portion of the shell, that are not coated with adhesive. The absorbent material portions are placed on the first portion of the shell and then the second portion of the shell is supplied from the second roll and laid on the first portion of the shell to cover the same area or in area-covering relationship and are pressed thereagainst in particular in the region of the adhesive coating. The above-mentioned steps can take place fully automatically in an automatic machine, wherein at the end of the production material sold by the meter leaves the machine and it is cut up as required. In a preferred embodiment the floor mat according to the invention has three absorbent segments, that is to say after each of the three absorbent portions a respective separation or cutting operation is performed.

Further advantages, features and possible uses of the present invention will be apparent from the description hereinafter of embodiments and the accompanying Figures.

Figure 1:
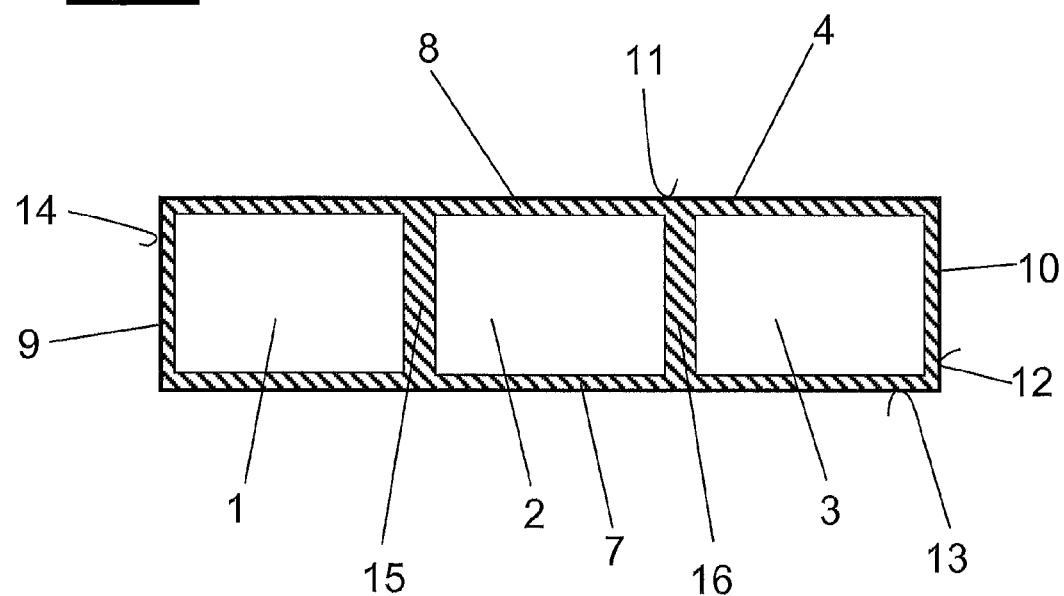
FIG. 1 shows a plan view of the floor mat according to the invention.

FIG. 1 shows a plan view of a floor mat according to the invention with three absorbent material portions 1, 2, 3 arranged in a common shell 4. In this arrangement the shell 4 has three mutually separate pockets in which the absorbent material portions 1, 2, 3 are arranged.

In the illustrated embodiment the absorbent material portions 1, 2, 3 comprise cellulose material with superabsorbent particles incorporated therein, based on sodium polyacrylate. Each of the absorbent material portions 1, 2, 3 is of a width of 32 cm and a length of 68 cm.

Figure 2:
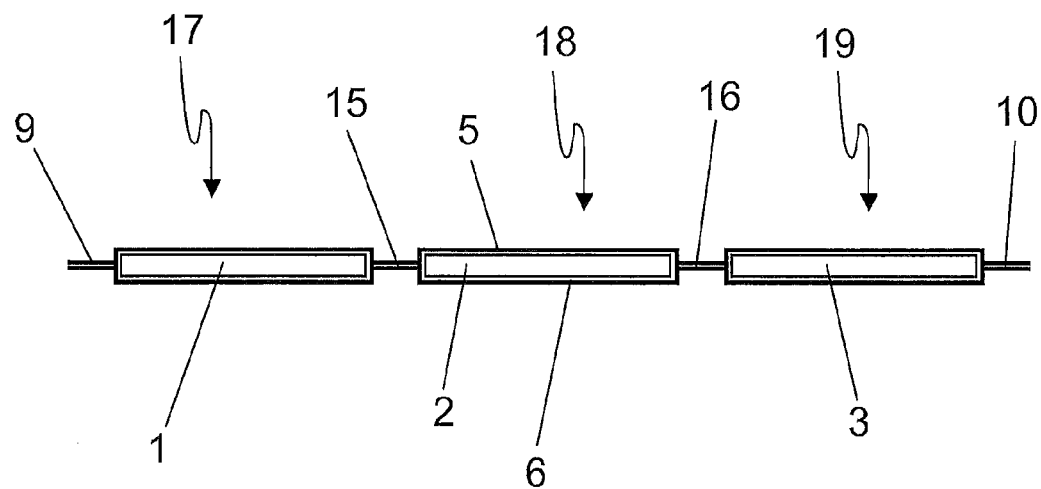
FIG. 2 shows a side view in section through the floor mat of FIG. 1.

As can be seen from the side view in section in FIG. 2 the shell 4 is formed by a lower material web 5 and an upper material web 6 which are glued together in portion-wise manner, forming the pockets in which the absorbent material portions 1, 2, 3 are accommodated. The shell 4 has two glued longitudinal seams 7, 8 and two glued transverse seams 9, 10 extending substantially parallel to the outside edges 11, 12, 13, 14 of the shell 4.

In addition the two material portions 5, 6 of the shell 4 are glued together in two further regions 15, 16. Those regions 15, 16 form the fold lines of the floor mat, along which the individual segments 1, 2, 3 of the mat can be folded onto each other.

It will be clear from the sectional view in FIG. 2 that those regions 17, 18, 19 of the floor mat, in which superabsorbent material portions 1, 2, 3 are arranged in the shell 4, are of a greater thickness than the portions 15, 16 of the fold lines.

In the illustrated embodiment the first and second portions 5, 6 of the shell are completely joined together in the regions 15, 16. In alternative embodiments, not shown here, in order to save adhesive the join between the webs 5, 6 of the sleeve could be effected only in portion-wise manner or punctiform manner, as long as separate pockets for the absorbent material portions 1, 2, 3 are afforded by the connection between the two material portions 5, 6 of the shell 4.

The length of the longitudinal side 11 of the illustrated floor mat is 73 cm while the widthwise side 12 measures 37 cm.

The thickness of the floor mat, measured in accordance with the standards of the European Norm EN 12625-3:1999, in the regions in which the superabsorbent material portions 1, 2, 3 are arranged, is 2 mm (first thickness) while in the regions of the fold lines 15, 16 it is 0.5 mm (second thickness).

The first and second portions 5, 6 of the shell 4 comprise a spunbond fabric of polypropylene fibers.

Figure 3:
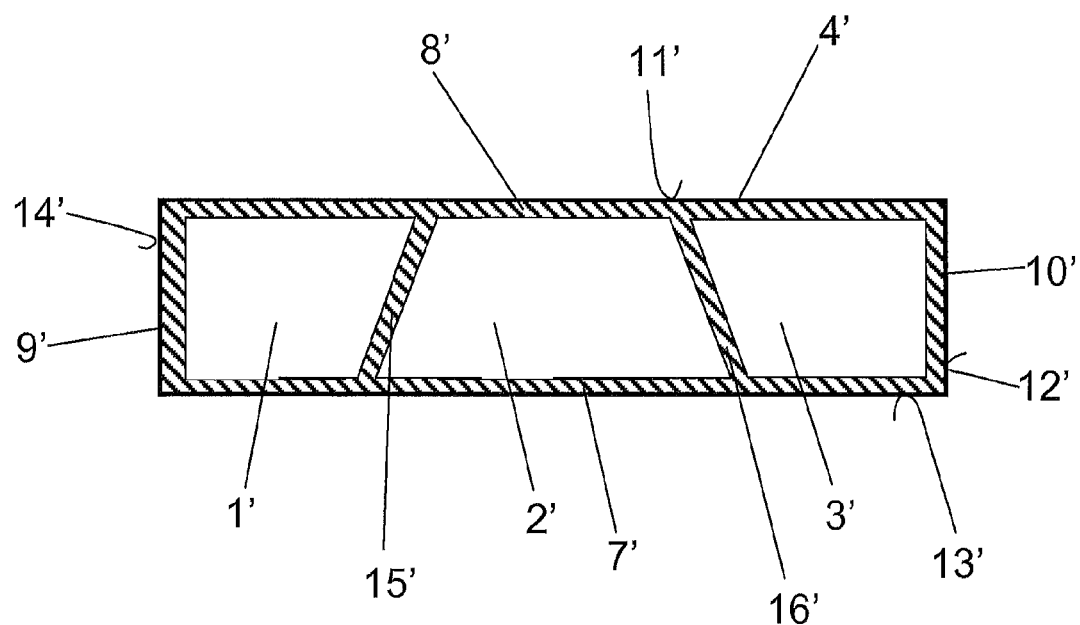
FIG. 3 shows a plan view of a further embodiment of the floor mat according to the invention.

FIG. 3 shows an alternative embodiment of the floor mat which also has three absorbent material portions 1', 2', 3'. In contrast to the FIG. 1 embodiment the fold lines 15' and 16' do not extend at a right angle to the outside edges 11', 13' of the mat but include an angle therewith. The central absorbent material portion 2' is thus of a trapezoidal shape. If now the segments of the mat which contain the absorbent material portions 1', 3' are folded along the fold lines 15', 16' onto the central absorbent material portion 2', that affords a U-shaped mat which can be arranged for example around the foot of an operating table.

For the purposes of the original disclosure it is pointed out that all features as can be seen by a man skilled in the art from the present description, the drawings and the claims, even if they are described in specific terms only in connection with certain other features, can be combined both individually and also in any combinations with others of the features or groups of features disclosed here insofar as that has not been expressly excluded or technical aspects make such combinations impossible or meaningless. A comprehensive explicit representation of all conceivable combinations of features is dispensed with here only for the sake of brevity and readability of the description.

While the invention has been illustrated and described in detail in the drawings and the preceding description that illustration and description is only by way of example and is not deemed to be a limitation on the scope of protection as defined by the claims. The invention is not limited to the disclosed embodiments.

Modifications in the disclosed embodiments are apparent to the man skilled in the art from the drawings, the description and the accompanying claims. In the claims the word "have" does not exclude other elements or steps and the indefinite article "a" does not exclude a plurality. The mere fact that certain features are claimed in different claims does not exclude the combination thereof. References in the claims are not deemed to be a limitation on the scope of protection.

| List of references | |
|---|---|
| 1, 2, 3, 1', 2', 3' | absorbent material portions |
| 4, 4' | shell |
| 5 | lower material web |
| 6 | upper material web |
| 7, 8, 7', 8' | longitudinal seams |
| 9, 10, 9', 10' | transverse seams |
| 11, 12, 13, 14 | outside edges of the shell |
| 11', 12', 13', 14' | outside edges of the shell |
| 15, 16, 15', 16' | fold lines |
| 17, 18, 19 | portions of the mat of the first thickness |

The invention claimed is:

1. A floor mat for absorbing fluids, the floor mat comprising:
a shell of a flexible non-woven spunbond fabric, said shell comprising a first portion and a second portion connected together portion-wise to form a pocket;
at least one absorbent material comprising a superabsorbent material arranged in said pocket;
said first and second shell portions having a length of 200 mm to 1000 mm and a width of 200 mm to 600 mm;
said first and second shell portions being connected together to form precisely three first portions of a first thickness and two second portions of a second thickness, each of said two second portions residing between two adjacent first portions to thereby form three spaced first portions;
said second thickness being less than said first thickness;
said second portions forming fold lines between adjacent first portions to enable said first portions to be pivotable toward each other;
said three first portions being configured with a narrow side and a wide side, said narrow sides being connected to said second portions to form the floor mat of alternating second thicknesses interconnecting absorbent filled said first portions which are at their narrow sides about said second thickness portions.

2. The floor mat as set forth in claim 1, wherein said first and second portions of said shell are rectangular.

3. The floor mat as set forth in claim 2, wherein said first and second portions of said shell are connected together at least portion-wise in such a way that they form the portions of the floor mat of the second thickness and thus said shell has three pockets, wherein said absorbent material is arranged in each of the pockets.

4. The floor mat as set forth in claim 1, wherein said first and second portions of said shell are connected together at least portion-wise in such a way that they form the portions of the floor mat of the second thickness and thus said shell has three pockets, wherein said absorbent material is arranged in each of the pockets.

5. The floor mat as set forth claim 1, wherein said first thickness is in a range of between 0.8 mm and 4.0 mm.

6. The floor mat as set forth in claim 1, wherein said second thickness is in a range of between 0.2 mm and 0.8 mm.

7. The floor mat as set forth in claim 1, wherein the ratio between said first thickness and said second thickness is in a range of between 1.5:1 and 20:1.

8. The floor mat as set forth in claim 1, wherein the connection between said first and second portions of said shell is an adhesive connection.

9. The floor mat as set forth in claim 1, wherein the connection between said first and second portions of said shell is an ultrasound welded connection.

10. The floor mat as set forth in claim 1, wherein the connection between said first and second portions of said shell is a thread seam.

11. The floor mat as set forth in claim 1, wherein said first thickness is in the range of between 1.2 mm and 3.0 mm.

12. The floor mat as set forth in claim 1, wherein said second thickness is in the range of between 0.4 mm and 0.6 mm.

13. The floor mat as set forth in claim 1, wherein the ratio between said first thickness and said second thickness is about 4:1.

* * * * *